United States Patent [19]
Murakami et al.

[11] Patent Number: 4,650,906
[45] Date of Patent: Mar. 17, 1987

[54] PROCESS FOR RECOVERING ETHYLENEAMINES FROM AQUEOUS SOLUTION OF ETHYLENEAMINE CARBONATES

[75] Inventors: Tsugio Murakami; Taizo Kawamoto, both of Shinnanyo, Japan

[73] Assignee: Toyo Soda Manufacturing Co., Ltd., Shinnanyo, Japan

[21] Appl. No.: 584,740

[22] Filed: Feb. 29, 1984

[30] Foreign Application Priority Data

Mar. 4, 1983 [JP] Japan ................................. 58-34650

[51] Int. Cl.$^4$ .............................................. C07C 85/26
[52] U.S. Cl. .................................... 564/498; 564/497; 564/478; 564/479; 564/482; 564/511; 564/512; 544/358; 544/402
[58] Field of Search ............... 564/497, 498, 482, 478, 564/511, 512, 479; 544/402, 358

[56] References Cited
U.S. PATENT DOCUMENTS
4,503,250 3/1985 Herdle ................................. 564/479

FOREIGN PATENT DOCUMENTS
0096571 12/1983 European Pat. Off. ............ 564/498
030805 3/1975 Japan ................................... 564/498
157520 12/1979 Japan ................................... 564/497

Primary Examiner—Charles F. Warren
Assistant Examiner—John A. Sopp
Attorney, Agent, or Firm—Oblon, Fisher, Spivak, McClelland & Maier

[57] ABSTRACT

Ethyleneamines are recovered from an aqueous solution of carbonates of ethyleneamines by distilling an aqueous solution of carbonates of ethyleneamines including ethylenediamine, in which the molar ratio of the carbon dioxide component to the ethyleneamines including ethylenediamine is 0.01 to 0.5, whereby ethylenediamine is distilled out together with water. The aqueous solution to be distilled is advantageously prepared by heating an aqueous solution of carbonates of ethyleneamines including ethylenediamine to effect decarboxylation.

17 Claims, No Drawings

PROCESS FOR RECOVERING ETHYLENEAMINES FROM AQUEOUS SOLUTION OF ETHYLENEAMINE CARBONATES

BACKGROUND OF THE INVENTION (1) Field of the Invention

This invention relates to a process for recovering ethyleneamines at a high efficiency from an aqueous solution of carbonates of ethyleneamines including ethylenediamine.

By the term "ethyleneamines including ethylenediamine" or "ethyleneamines" used in the instant specification is meant ethylenediamine alone or a mixture of ethylenediamine with other ethyleneamines, unless otherwise indicated. Furthermore, the term "polyamine" is used for indicating said other ethyleneamines.

As the polyamine, there can be mentioned linear and cyclic ethyleneamines such as diethylenetriamine, triethylenetetramine, tetraethylenepentamine, pentaethylenehexamine, tris-(2-aminoethyl)-amine, piperazine and N-aminoethylpiperazine. These polyamines may be present either alone or in combination in the aqueous solution to be treated by the process of the present invention. The amount or concentration of ethyleneamines is the sum of the amount or concentration of free ethyleneamines and the amount or concentration of ethyleneamine carbonates calculated as free ethyleneamines.

(2) Description of the Prior Art

Ethyleneamines are widely used in various fields as primary raw materials, secondary raw materials or additives. For example, they are used for agricultural chemicals, paper strength improvers, epoxy curing agents, lubricant additives, and in the production of polyamides. Among ethyleneamines, ethylenediamine is most widely used in various fields because of its high basicity and reactivity and because the available product thereof is of a high purity.

These ethyleneamines are usually produced by the following two methods, although the ethyleneamines referred to in the present invention are not limited to those prepared by these methods.

(a) EDC Method

Ethylene dichloride (EDC) is reacted with ammonia at high temperature and high pressure to form ethyleneamine hydrochlorides. These hydrochlorides are subjected to double decomposition with sodium hydroxide, and the sodium chloride by-product is separated from the decomposition product.

(b) MEA Method

Monoethanolamine (MEA) is reacted with ammonia in the presence of a hydrogenation catalyst at high temperature and high pressure to obtain ethyleneamines.

Carbonates of ethyleneamines are formed, for example, in the process for the preparation of ethyleneamines or when, in a reaction using ethyleneamines, unreacted ethleneamines are reacted with carbon dioxide to recover the ethyleneamines in the form of ethyleneamine carbonates.

For example, carbonates of ethyleneamines are formed when ethyleneamines are selectively extracted from an aqueous solution containing ethyleneamines and the ethylene amines are recovered as carbonates from the extracted organic phase by using carbon dioxide gas or aqueous carbonic acid, as disclosed in European Patent Application No. 0096571-A2. Incidentally, the carbonates of ethyleneamines are fundamentally reaction products between ethyleneamines and carbon dioxide, and they are called ethyleneamine carbamates in some cases.

Carbonates of ethyleneamines containing ethylenediamine are sometimes used as commercial products as such, but in many cases, they are marketed after they are rendered free from the carbonate group, that is, as free ethylenediamines, and are separated into respective components. Accordingly, the carbonates of ethyleneamines should be subjected to decarboxylation, and ethylenediamine is separated from the decarboxylated product.

For this decarboxylation, there may be considered a method in which double decomposition is effected by addition of a strong alkali such as sodium hydroxide or calcium hydroxide and then, sodium carbonate or calcium carbonate formed as a by-product is separated from ethyleneamines. This method, however, is commercially disadvantageous because a large amount of the strong alkali should be used and the treatment of the carbonate formed as a by-product is necessary.

We researched toward developing a method capable of performing the decarboxylation at a high efficiency without using an alkali such as sodium hydroxide or calcium hydroxide. As the result, it was found that decarboxylation can be performed by heating an aqueous solution of ethyleneamine carbonates containing ethylenediamine. However, it was found that if the aqueous solution is merely heated, the rate of decarboxylation is reduced with advance of decarboxylation and the decarboxylation reaction is stopped in the state where the carbon dioxide component (hereinafter referred to as "$CO_2$ component") is left in a large quantity. It also was found that this tendency is conspicuous when the concentration of the carbonates of ethyleneamines is high or the content of ethylenediamine is high.

SUMMARY OF THE INVENTION

It is a primary object of the present invention to provide a process for recovering ethyleneamines from an aqueous solution whereby the ethyleneamines can be recovered in a high yield and in an advantageous manner.

Another object of the present invention is to provide a process for recovering ethyleneamines from an aqueous solution of carbonates of ethyleneamines by decarboxylation under heating which process is resource-saving and simplified.

Other objects and advantages of the present invention will be apparent from the following description.

More specifically, in one aspect of the present invention, there is provided a process for recovering ethyleneamines from an aqueous solution of carbonates of ethyleneamines, which comprises distilling an aqueous solution of carbonates of ethyleneamines including ethylenediamine, in which the molar ratio of the carbon dioxide component to the ethyleneamines including ethylenediamine is in the range of from 0.01 to 0.5, whereby ethylenediamine is distilled out together with water.

In another aspect of the present invention, there is provided a process for recovering ethyleneamines from an aqueous solution of ethyleneamine carbonates, which comprises heating an aqueous solution of carbonates of ethyleneamines including ethylenediamine to effect decarboxylation and then distilling the aqueous solution, whereby ethylenediamine is distilled out together with water.

DESCRIPTION OF THE PREFERRED EMBODIMENTS

The present invention is directed to a process for recovering ethylenediamine in the free state from an aqueous solution of carbonates of ethyleneamines including ethylenediamine. Moreover, the present invention is directed to a process for recovering a polyamine in the free state from an aqueous solution containing a carbonate of a polyamine in addition to a carbonate of ethylenediamine.

As pointed out hereinbefore, we carried out various trials to effect decarboxylation under heating of aqueous solutions of carbonates of ethyleneamines, and found that decarboxylation is easy when the concentration of ethyleneamine carbonates is low, the ethylenediamine content is low or the ratio of primary amines in the amino groups of ethyleneamines is low. In other words, decarboxylation is difficult as the concentration of ethyleneamine carbonates is high, the ethylenediamine content is high and the ratio of primary amines in the amine groups is increased. In view of these findings, it was considered impossible to obtain ethylenediamine by decarboxylation under heating of carbonates of ethyleneamines.

However, as the result of our further research and investigation, we found a very interesting fact. Namely, it was found if decarboxylation of an aqueous solution of carbonates of ethyleneamines is carried out under heating and distillation is then carried out in the state where the $CO_2$ component is present, ethylenediamine having a highest basicity can be distilled out together with water without distillation of carbon dioxide gas, while the $CO_2$ component in the bottom residue is concentrated with an increase in the amounts of distilled ethylenediamine and water. It is construed that the reason is probably as follows.

When the concentration of ethylenediamine distilled out at the distillation step is compared with the concentration of ethyleneamines in the bottom residue, the concentration of ethyleneamines in the bottom residue is always higher. The basicity of ethyleneamines greatly varies depending upon the concentration thereof and the higher the concentration, the higher is the basicity. Furthermore, the basicity in the solution state is higher than the basicity in the gaseous state. Accordingly, it is considered that the $CO_2$ component is selectively retained in the bottom residue. Incidentally, even if the bottom residue is a polyamine having a lower basicity than that of ethylenediamine, the $CO_2$ component is strongly retained in the bottom residue. It is considered that the reason is that the concentration of the polyamine is high and the polyamine is in the solution state.

According to the present invention, even though decarboxylation of an aqueous solution of carbonates of ethyleneamines including ethylenediamine is not completely performed, free ethylenediamine can be recovered. For this purpose, it is indispensable, except for an especial case, that decarboxylation under heating be carried out in advance.

By heating an aqueous solution of ethyleneamine carbonates, carbon dioxide gas is volatilized and free ethyleneamines are formed. However, as pointed out hereinbefore, complete decarboxylation is not accomplished only by heating.

It is ordinarily preferred that decarboxylation be carried out under atmospheric pressure, because the operation and apparatus employed may be simple. It is preferred that the temperature adopted at this step be in the range of from 80° to 120° C. Decarboxylation is advanced more rapidly as the temperature is higher. Accordingly, the decarboxylation may be carried out at a high temperature under an elevated pressure. Generally, the decarboxylation temperature is in the range of from 120° to 200° C. This temperature is usually attained at a gauge pressure of from 1 to 8 kg/cm$^2$·G. It also is preferred that the decarboxylation be carried out under boiling. The reason is that the partial pressure of carbon dioxide is reduced by boiling whereby the decarboxylation is accelerated. In this case, volatilized ethyleneamines and water are condensed and recycled to the bottom residue. The decarboxylation is further advanced if at least one member selected from steam, nitrogen gas and air is introduced into the aqueous solution of carbonates of ethyleneamines.

It is preferred that the concentration of ethyleneamines be in the range of from 200 to 600 g/l. If this concentration is too low, the decarboxylation is advanced, but a large quantity of energy becomes necessary for removing water. If the concentration is too high, it is impossible to perform the decarboxylation sufficiently, and the yield of ethylenediamine is reduced at the subsequent step of distillation of ethylenediamine.

It is preferred that the content of ethylenediamine in the ethyleneamines be at least 10% by weight, more preferably at least 20% by weight. If this content is low, the decarboxylation is efficiently advanced but the amount of the liquid to be treated per unit weight of ethylenediamine is increased.

We performed the decarboxylation of (A) an aqueous solution of an ethylenediamine carbonate, (B) an aqueous solution of a mixture of carbonates of ethylenediamine and polyamine and (C) an aqueous solution of a carbonate of a polyamine under the same conditions, and the carbon dioxide removal ratios were compared. It was found that the carbon dioxide removal ratio in the decarboxylation (B) is much higher than the carbon dioxide removal ratio in the decarboxylation (A) and (C), provided that the concentration of ethyleneamine in each solution is the same. The reason for this fact is not clear, but, it is presumed that, in the decarboxylation of a mixed solution of carbonates of ethylenediamide and polyamine, polyamine carbonate of a weak basicity is initially decomposed and then ethylenediamine carbonate is decomposed. However, ethylenediamine has a strong basicity and exhibits enhanced retention of the $CO_2$ component. Accordingly, if the amount of polyamine carbonate in the mixed solution is minor, the decomposition of ethylenediamine advances only at a reduced rate. In contrast, if a relatively large amount of polyamine carbonate is contained in the mixed solution, a part of the $CO_2$ component retained by ethylenediamine becomes retained by polyamine and hence readily decomposed, and the $CO_2$ removal ratio is enhanced. The carbon dioxide removal ratio is high as the polyamine content is high, and this removal ratio is especially high when the ethylenediamine content is not higher than 80% by weight. Therefore, it is preferred that the ethylenediamine content in ethyleneamines be not higher than 80% by weight, more preferably in the range of from 20 to 80% by weight.

If the decarboxylation is carried out in the presence of an alcohol or ether, the decarboxylation is further advanced. An alcohol having 3 to 5 carbon atoms, especially 4 carbon atoms, is preferred. Dioxane is effective as the ether.

The decarboxylation under heating may be carried out batchwise or in a continuous manner, and a distillation column of multiple stages may be used.

The decarboxylation of an aqueous solution of carbonates of ethyleneamines is performed in the above-mentioned manner. If the subsequent distillation is taken into consideration, the molar ratio of the $CO_2$ component to ethyleneamines be reduced to a value in the range of from 0.01 to 0.5, though the preferred molar ratio differs to some extent according to the conditions and time. Ordinarily, this reduction of the molar ratio can easily be accomplished.

In the process of the present invention, after the decarboxylation under heating of carbonates of ethyleneamines, distillation is carried out, whereby ethylenediamine is distilled out together with water.

When an aqueous solution of carbonates of ethyleneamines is subjected to distillation without the decarboxylation under heating, carbon dioxide gas is distilled out together with ethylenediamine and reacts with ethylenediamine. Accordingly, the recovered product is a carbonate of ethylenediamine.

The distillation may be simple distillation or multi-staged distillation including rectification. The latter distillation process is preferred so as to obtain ethylenediamine having a higher purity. The distillation may be carried out batchwise or in a continuous manner. Since ethylenediamine having a higher purity is obtained as the distillation temperature is lower, it is preferred that the pressure is reduced below atmospheric pressure to prevent elevation of the temperature. If the pressure is elevated, the temperature is elevated and parts of carbonates of ethyleneamines are decomposed and carbon dioxide gas is distilled out and the purity of ethylenediamine is reduced.

The temperature may be elevated as the concentration of ethyleneamines is high or the ethylenediamine content is high. However, it is preferred that the temperature be not higher than 150° C., especially not higher than 115° C.

When an aqueous solution of ethyleneamines containing a small amount of the $CO_2$ component left undecomposed is distilled, ethylenediamine is distilled out together with water, while an aqueous concentrated solution of carbonates of ethyleneamines is left as the bottom residue.

The yield of ethylenediamine recovered by distillation differs according to the concentration of ethyleneamines to be distilled, the composition of ethyleneamines, the concentration of the $CO_2$ component, the distillation temperature and other conditions. The yield of ethylenediamine is increased when the concentration of ethyleneamines is low, the content of ethylenediamine is low, the concentration of the $CO_2$ component is low or the distillation temperature is low. Ordinarily, distillation is conducted until the amount of ethyleneamines in the bottom residue is equimolar to the amount of the $CO_2$ component. It is preferred that the distillation be carried out so that the molar ratio of the $CO_2$ component to ethyleneamines in the bottom residue is in the range of from 0.3 to 0.8.

If the molar ratio of the $CO_2$ component in the aqueous solution of carbonates of ethyleneamines is low, for example, if the molar ratio of the $CO_2$ component to ethyleneamines is not higher than 0.5, ethylenediamine can directly be obtained together with water by distillation without the decarboxylation under heating.

If the free ethyleneamines and ethyleneamines in the carbonates are composed of ethylenediamine alone, ethylenediamine is distilled out together with water by distillation, and the bottom residue becomes an aqueous concentrated solution of an ethylenediamine carbonate. If it is intended to obtain ethylenediamine by further distillation, a part of ethylenediamine carbonate in the bottom residue is decomposed and carbon dioxide gas is distilled out. Accordingly, all of ethylenediamine cannot completely be recovered by distillation. The amount of ethylenediamine retained in the bottom residue is decreased when the amount of the $CO_2$ component is small, the distillation temperature is low or the concentration of ethylenediamine in the bottom residue is high. Ordinarily, ethylenediamine may be reduced to an amount substantially equimolar to the amount of the $CO_2$ component. It is preferred that ethylenediamine be left in an amount of about 1 to about 3 moles per mole of the $CO_2$ component. Since the basicity of ethylenediamine is high, even if the temperature is high, the $CO_2$ component can be retained to a large extent, but it is preferred that the temperature be not higher than 150° C. If it is desired to recover all of ethylenediamine by distillation, the aqueous concentrated solution of the ethylenediamine carbonate left as the bottom residue is recycled to the preceding step of the decarboxylation under heating.

If the free ethyleneamines and ethyleneamines in the carbonates are composed of a mixture of ethylenediamine and a polyamine, all of ethylenediamine can substantially be recovered by distillation. The reason is that the $CO_2$ component left after the decarboxylation under heating can be retained in the polyamine as the polyamine carbonate in the bottom residue. This is one of the advantages of the present invention.

Ethylenediamine has the highest basicity and ethylenediamine forms a carbonate with the $CO_2$ component in the solution. However, it is considered that if ethylenediamine is distilled out by distillation, the polyamine forms a carbonate with the $CO_2$ component as indicated by the following formula:

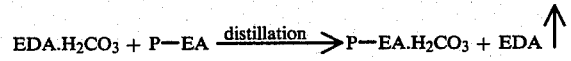

$$EDA \cdot H_2CO_3 + P-EA \xrightarrow{distillation} P-EA \cdot H_2CO_3 + EDA \uparrow$$

wherein EDA is ethylenediamine and P-EA is the polyamine.

In this case, the amount of the $CO_2$ component retained in the polyamine varies according to the kind and concentration of the polyamine and the temperature. Namely, the amount of the $CO_2$ component retained in the polyamine is increased when the polyamine has more primary amine content, the concentration of the polyamine is more or the distillation temperature is lower. The influence of the temperature is most significant, and if the temperature is not higher than 115° C., the $CO_2$ component can be retained in an amount substantially equimolar to the amount of the polyamine. In order to obtain ethylenediamine having a high purity, it is preferred that the $CO_2$ component be retained in an amount of 0.3 to 0.8 mole per mole of the polyamine. When the temperature is higher than 115° C., especially higher than 120° C., it becomes difficult to retain the $CO_2$ component in a large amount in the polyamine.

This is an important fact found for the first time by us. Therefore, in order to retain the $CO_2$ component in a larger amount in the polyamine, it is preferred that the operation be carried out under a reduced pressure lower than atmospheric pressure, and the temperature can easily be reduced to 115° C. or lower. It is preferred that the temperature be in the range of from 80° to 115° C. Furthermore, it is possible to retain the $CO_2$ component not only in the polyamine but also in ethylenediamine, and in this case, a part of ethylenediamine is retained in the bottom residue. If the distillation is carried out at a temperature higher than 115° C., it becomes difficult to retain the $CO_2$ component in a large amount in the polyamine, and therefore, a part of ethylenediamine is left in the bottom residue and the $CO_2$ component is retained in this ethylenediamine.

Accordingly, the bottom residue is an aqueous concentrated solution of the polyamine carbonate in one case, and the bottom reside is an aqueous concentrated solution of the ethylenediamine carbonate and polyamine carbonate in the other case.

Namely, in case of an aqueous solution of a polyamine carbonate, if the decarboxylation under heating is carried out at a temperature higher than 115° C., especially higher than 120° C., the decarboxylation is accomplished substantially completely and free polyamine can be obtained. A part of the obtained free polyamine may be recycled to the preceding distillation step. By this recycle, a larger amount of the $CO_2$ component can be retained in the polyamine, and the conditions for the decarboxylation under heating, which is conducted prior to the distillation, can be conducted under moderate conditions.

In case of an aqueous solution of an ethylenediamine carbonate and polyamine carbonates, the decarboxylation under heating is preferably carried out at a temperature higher than 115° C., especially higher than 120° C. If ethylenediamine, water and carbon dioxide, vaporized at this step, are recycled to the first decarboxylation under heating, which is precedent to the distillation, without condensation, all of ethylenediamine can be recovered substantially completely, and the polyamine is obtained in the free state at the decarboxylation under heating, which is conducted after the distillation. A part of the obtained polyamine may be recycled to the distillation step, or to the decarboxylation step precedent to the distillation step. Furthermore, at this step of the decarboxylation under heating, an organic solvent may be used. An alcohol having 3 to 5 carbon atoms or a cyclic ether may be used as the organic solvent. An alcohol having 4 carbon atoms or dioxane is especially preferred. In this case, the decarboxylation is completed within 1 hour. In some cases, a very small amount of the $CO_2$ component is left in the polyamine after this decarboxylation under heating. In such cases, it is preferred that a strong alkali such as sodium hydroxide be used in an amount larger than the equimolar amount to the $CO_2$ component. The $CO_2$ component can be separated in the form of a carbonate such as sodium carbonate.

Ethylenediamine can be recovered together with water from an aqueous solution according to the above-mentioned procedures, and polyamines can also be recovered.

In the case where it is intended to obtain only ethylenediamine from ethylenediamine and water, the conventional dehydration process comprising dehydration under an elevated pressure alone or in combination with dehydration under atmospheric pressure may be adopted.

Advantages attained by the process of the present invention are as follows.

(1) Since ethylenediamine can be recovered from an aqueous solution of ethyleneamine carbonates by heating and distillation, chemicals such as calcium hydroxide or sodium hydroxide need not be used and a resource-saving effect can be attained.

(2) The operation is simple.

(3) A polyamine contained in ethyleneamines can be obtained in the free state.

(4) An aqueous solution of ethyleneamine carbonates having a high concentration can be treated.

The present invention will now be described in detail with reference to the following examples and comparative examples.

EXAMPLE 1

A 1-liter volume four-necked round-bottom flask equipped with a reflux cooler was charged with 500 ml of an aqueous solution containing 200 g/l of ethylenediamine (EDA) and 145 g/l of $CO_2$. Decarboxylation was conducted for 5 hours at a boiling point of 104° C. by using a mantle heater of 300 W as the heat source according to the full reflux method. Thus, there was obtained an aqueous solution containing 205 g/l of EDA and 19 g/l of $CO_2$. Then, 100 ml of the aqueous solution was charged in a 200-ml volume four-necked round-bottom flask equipped with a cooling pipe and a rectifying column (filler: glass ring having a diameter of 2 mm, filling height: 200 mm, inner diameter: 20 mm). Distillation was carried out by using a mantle heater of 210 W. The distillation was terminated when 85 ml of the distillate was obtained. The distillate contained 132 g/l of EDA and 0.12 g/l of $CO_2$. At the time of termination of the distillation, the temperature of the bottom residue was 123° C., the amount of the bottom residue was 5.0 ml, and the bottom residue contained 650 g/l of EDA and 350 g/l of $CO_2$.

EXAMPLE 2

Reduced pressure distillation of 100 ml of the aqueous solution obtained at the decarbosylation under heating in the distillation apparatus used in Example 1 was carried out while nitrogen gas was introduced at a rate of 10 ml/min under an absolute pressure of 100 mmHg attained by an aspirator.

The distillation was terminated when 88 ml of the distillate was obtained. The distillate contained 148 g/l of EDA and less than 20 mg/l of $CO_2$. The temperature of the bottom residue at the time of termination of the distillation was 75° C., the amount of the bottom residue was 4.4 ml, and the bottom residue contained 670 g/l of EDA and 410 g/l of $CO_2$.

EXAMPLE 3

The opearation of recycling the concentrated aqueous solution of the ethylenediamine carbonate left as the bottom residue in Example 2 to the step of the decarboxylation under heating was conducted after the operation of Example 2. All of EDA contained in the starting aqueous solution of the ethylenediamine carbonate could be substantially completely recovered in the substantially $CO_2$-free state together with water by the distillation.

EXAMPLE 4

In the same manner as described in Example 1, 500 ml of an aqueous solution containing 140 g/l of EDA, 7.6 g of piperazine (P), 92 g/l of diethylenetriamine (DETA), 13 g/l of N-aminoethylpiperazine (N-AEP), 55 g/l of triethylenetetramine (TETA), 25 g/l of tetraethylenepentamine (TEPA), 18 g/l of pentaethylenehexamine (PEHA) and 217 g/l of $CO_2$ was subjected to decarboxylation under heating at a boiling point of 105° C. Thus, an aqueous solution of ethyleneamines containing 18 g/l of $CO_2$ was obtained. Then, 100 ml of the aqueous solution was distilled under reduced pressure in the same manner as described in Example 2. The distillation was terminated when 68 ml of the distillate was obtained. The distillate contained 139 g/l of EDA and less than 20 mg/l of $CO_2$ The temperature of the bottom residue at the time of termination of the distillation was 104° C. and the bottom residue was substantially free of EDA. Namely, 25 ml of the bottom residue containing 850 g/l of the polyamine mixture and 71 g/l of $CO_2$ was obtained.

EXAMPLE 5

A 50-ml volume three-necked round-bottom flask equipped with reflux cooler was charged with 20 ml of the bottom residue obtained by the distillation operation in Example 4. Decarboxylation was carried out at a boiling point of 136° C. for 30 minutes according to the full reflux method by using a mantle heater as the heat source. Thus, an aqueous solution containing 860 g/l of the polyamine mixture and 4.3 g/l of $CO_2$ obtained.

EXAMPLE 6

In the same manner as described in Example 1, 500 ml of an aqueous solution containing 168 g/l of EDA, 6.3 g/l of P, 77 g/l of DETA, 11 g/l of N-AEP, 46 g/l of TETA, 21 g/l of TEPA, 15 g/l of PEHA and 214 g/l of $CO_2$ was subjected to decarboxylation at a boiling point of 104° C. to obtain an aqueous solution of ethyleneamines containing 27 g/l of $CO_2$. Then, 150 ml of the aqueous solution was subjected to distillation under atmospheric pressure in the same manner as described in Example 1. The distillation was terminated when 96 ml of the distillate was obtained. The distillate contained 135 g/l of EDA and 0.10 g/l of $CO_2$. The temperature of the bottom residue at the time of termination of the distillation was 131° C. The amount of the bottom residue was 46 ml and the bottom residue contained 180 g/l of EDA, 580 g/l of the polyamine mixture and 85 g/l of $CO_2$.

EXAMPLE 7

A 50-ml volume three-necked round-bottom flask was charged with 40 ml of the bottom residue obtained by the distillation operation in example 6 was subjected to decarboxylation under heating at 136° C. for 30 minutes by using a mantle heater as the heat source.

An aqueous solution containing 850 g/l of a polyamine mixture and 4.0 g/l of $CO_2$, which was substantially free of EDA, was obtained. Incidentally, the solidified ethylenediamine carbonate adhered to the cooler.

EXAMPLE 8

To 1 liter of an aqueous solution containing 90 g of EDA and 180 g of sodium chloride was added 1 liter of a n-butanol solution containing 330 ml of cyclohexanone. The mixture was shaken for 10 minutes and was then subjected to stationary separation.

Then, 200 ml of pure water was added to 800 ml of the organic phase containing 60.0 g/l of EDA, which was obtained by the stationary separation, and water-saturated carbon dioxide gas was blown at a rate of 300 ml/min for 4 hours to obtain an aqueous solution of ethylenediamine carbonate containing 196 g/l of EDA and 140 g/l of $CO_2$. In the same manner as described in Example 1, 200 ml of the aqueous solution of the ethylenediamine carbonate was subjected to decarboxylation under heating and distillation under atmospheric pressure to obtain 86 ml of a distillate containing 130 g/l of EDA and 0.14 g/l of $CO_2$.

COMPARATIVE EXAMPLE 1

In the same manner as described in Example 1, 100 ml of an aqueous solution containing 200 g/l of EDA and 145 g/l of $CO_2$ was subjected to distillation. A large amount of carbon dioxide gas was formed and an aqueous solution of ethylenediamine carbonate was obtained as the distillate.

We claim:

1. A process for recovering ethylenediamine from an initial aqueous solution of carbonates of ethylenediamine alone or in admixture with other ethyleneamines, which comprises distilling an initial aqueous solution of the carbonates in which the molar ratio of the carbon dioxide component to the total ethyleneamine content is in the range of from 0.01 to 0.5, whereby ethylenediamine is distilled out together with water while retaining an ethyleneamine bottom residue containing substantially all of the carbon dioxide.

2. A process according to claim 1, wherein the distillation is carried out at a temperature not higher than 150° C.

3. A process according to claim 1, wherein the distillation is carried out at a temperature not higher than 115° C.

4. A process for recovering ethylenediamine from an aqueous solution of carbonates of ethylenediamine alone or in admixture with other ethyleneamines, which comprises heating the aqueous solution to effect partial decarboxylation of the aqueous solution while retaining substantially all of the ethyleneamines, and the distilling the partially decarboxylated aqueous solution, whereby ethylenediamine is distilled out together with water while retaining an ethyleneamine bottom residue containing substantially all of the carbon dioxide, the molar ratio of the carbon dioxide component to the total ethyleneamines in the partially decarboxylated aqueous solution being in the range of from 0.01 to 0.5.

5. A process according to claim 4, wherein the ethylenediamine content in the ethyleneamine admixture is in the range of from 20 to 80% by weight.

6. A process according to claim 4, wherein at least one member selected from the group consisting of steam, nitrogen gas or air is introduced at the step of the decarboxylation by heating.

7. A process according to claim 4, wherein the decarboxylation by heating is effected at a temperature of 80° to 200° C.

8. A process according to claim 4, wherein the decarboxylation by heating is effected under boiling while volatilized ethyleneamines and water are condensed and recycled to the aqueous solution.

9. A process according to claim 4, wherein the concentration of the ethyleneamines in the aqueous solution is in the range of from 200 to 600 g/l.

10. A process according to claim 4, wherein the decarboxylation by heating is effected in the presence of an alcohol of 3 to 5 carbon atoms or an ether.

11. A process according to claim 4, wherein the decarboxylation by heating is effected in the presence of an alcohol of 4 carbon atoms or dioxane.

12. A process according to claim 4, wherein the distillation is carried out at a temperature not higher than 150° C.

13. A process according to claim 4, wherein the distillation is carried out at a temperature not higher than 115° C.

14. A process according to claim 4, wherein the aqueous solution of the carbonates is an aqueous solution of ethylenediamine carbonate, and the bottom residue left after the distillation is recycled to the step of the decarboxylation by heating.

15. A process according to claim 4, wherein the aqueous solution of the carbonates is an aqueous solution of ethylenediamine carbonate and polyamine carbonates, and the bottom residue left after the distillation is subjected to decarboxylation at a temperature of higher than 115° C.

16. A process according to claim 15, wherein a vapor comprising as main components ethylenediamine, carbon dioxide gas and water, which is formed by the decarboxylation of the bottom residue left after the distillation at a temperature higher than 115° C., is recycled to the step of the decarboxylation of the aqueous solution of the carbonates.

17. A process according to claim 4, wherein the distillation is carried out so that the molar ratio of the $CO_2$ component to the total ethyleneamine content in the bottom residue is in the range of from 0.3 to 0.8.

* * * * *